United States Patent [19]

Taylor

[11] Patent Number: 5,509,916
[45] Date of Patent: Apr. 23, 1996

[54] LASER-ASSISTED ELECTROSURGERY SYSTEM

[75] Inventor: Kenneth D. Taylor, Broomfield, Colo.

[73] Assignee: Valleylab Inc., Boulder, Colo.

[21] Appl. No.: 289,958

[22] Filed: Aug. 12, 1994

[51] Int. Cl.$^6$ .................................................. A61B 17/32
[52] U.S. Cl. .............................. 606/13; 606/10; 606/41; 606/42; 606/33
[58] Field of Search .............................. 606/2, 3, 10–17, 606/32–34, 37–42, 45–52

[56] References Cited

U.S. PATENT DOCUMENTS

| | | |
|---|---|---|
| 4,781,175 | 11/1988 | McGreevy et al. |
| 5,011,483 | 4/1991 | Sleister .................................... 606/41 |
| 5,192,278 | 3/1993 | Hayes et al. .............................. 606/15 |
| 5,304,176 | 4/1994 | Phillips .................................... 606/41 |
| 5,324,254 | 6/1994 | Phillips . |
| 5,401,272 | 3/1995 | Perkins .................................... 606/15 |

FOREIGN PATENT DOCUMENTS

| | | |
|---|---|---|
| 57-69853 | 4/1982 | Japan . |
| 57-69790 | 4/1982 | Japan . |

OTHER PUBLICATIONS

Zhau et al, "How Lasers Might Control Lightning Strikes", Laser Focus World, Nov. 1993, pp. 113–123.

*Primary Examiner*—Stephen C. Pellegrino
*Assistant Examiner*—Michael Peffley
*Attorney, Agent, or Firm*—Peter C. Richardson; Lawrence C. Akers; Aaron Passman

[57] ABSTRACT

A laser and electrosurgical system has a handpiece with a proximal and distal end from which laser radiation and/or electrosurgical energy is selectively or concurrently directed. The ends are along an axis; an electrode extends distally along the axis. Sources of laser and electrosurgical energy are available and controlled. An initiation circuit for the laser selectively delivers it before electrosurgery. Prior delivery targets tissue. The laser creates an ionized conductive pathway for electrosurgery. The combined concurrent application of laser and electrosurgery has a mechanism to selectively distribute energy about the axis. A laser deflecting surface or a beam deflector vibrate relative to the axis. A power switch has levels for laser cut and ionization and/or a delay therebetween for electrosurgical coagulation. A wave guide or an array thereof deliver radiation along the axis. A method has steps of directing selectively and concurrently laser and electrosurgery by aiming the axis, controlling laser and electrosurgical energy, delivering laser before electrosurgery, forming an ionized conductive pathway for the electrosurgery, distributing the laser about the axis in a predetermined pattern by deflecting the laser in a predetermined pattern generally along but slightly displaced from the axis to direct electrosurgical energy in a predefined pattern on the patient's target tissue. In another possible approach, there are additional steps of delivering the laser radiation as a beam and varying an ionized conductive pathway by refracting or diffracting the laser radiation beam with the mechanism having a beam pattern deflector.

7 Claims, 5 Drawing Sheets

LASER-ASSISTED ELECTROSURGERY SYSTEM

FIELD OF THE INVENTION

This invention relates to electrosurgery combined with laser radiation in a single surgical instrument, and more particularly the selective and/or concurrent delivery from a surgical handpiece of laser energy and electrosurgery with superior benefits to those available separately.

BACKGROUND OF THE DISCLOSURE

Electrosurgery involves the application of radio frequency energy to achieve a tissue effect. The electrosurgical energy is generated by an electrosurgical generator which is applied to the tissue either by monopolar or bipolar circuits. In monopolar, there is a small active electrode directed toward the tissue to be treated and to complete the circuit there is a large patient return electrode applied somewhere to the patient's body. The power density through the patient return electrode is relatively small so that there is no tissue effect thereat. In bipolar, a pair of electrodes are spaced close together with tissue therebetween. In certain circumstances the bipolar electrodes are moveable toward and away from one another.

Electrosurgery can be used for cutting, coagulating or a combination thereof called blend. Coagulation is often described as desiccation of the tissue and fulguration of the tissue. Fulguration is the electrical arcing from the active electrode toward various locations, on the patient's tissue, in the vicinity of the active electrode. Typically when the arcs travel through air, they reach the tissue in a random, nonpredictable manner. In many cases arcs leave the active electrode in a trajectory emanating generally along the axis of the active electrode, but before they contact the tissue their paths may vary due to the impedance at the tissue near the active electrode. The resulting fulguration is an uneven or randomly concentrated or irregularly distributed delivery of the energy in each arc, thus producing an uneven or variable coagulation of the tissue desiccated thereat. This is unsatisfactory from the point of view of producing a controlled and preferred level of eschar.

Ionized gases have been used to direct the electrosurgical energy in a more controlled manner. U.S. Pat. No. 4,781,175 deals particularly with that approach. A disadvantage of using ionized gas is the possibility of formation of embolisms within the blood of the patient being treated. In addition, there is the potential for the gas being misdirected and forming a plasma torch either through a leak in the electrosurgical handpiece or pencil or when delivered in a laparoscopic procedure within the trocar which provides entry into the body cavity. Another problem with ionized gas is that the electrosurgery and the gas flow are essentially concurrent in the form of a plasma flame that is used to fulgurate and desiccate tissue at which it is aimed. The aiming or positioning of the plasma flame on the desired target tissue is uncertain until activated. Therefore, the pinpointing of the spot at which to initiate the effect is not readily determinable until the electrosurgical energy is delivered.

U.S. Pat. No. 5,011,483 discloses a device which is in the form of a handpiece housing from which electrosurgical and laser energy may be delivered alternatively for selective use thereof. In connection with laparoscopic procedures, an elongate hollow shaft is disclosed for a wave guide to conduct the laser energy. The wave guide may be flexible and one preferred form is a fiber optic. The disclosure of the reference is largely limited to the alternate use of laser or electrosurgery. There is no discussion or disclosure of concurrent delivery.

Japanese patent JP57-69853 relates to a laser device which radiates a laser beam to mark the position for subsequent application of laser surgery. No electrosurgery is disclosed and the use of a laser with electrosurgery even for pinpointing is not taught. Japanese patent JP57-69790 has a laser radiation apparatus with a laser oscillator including a light guide and a generator for radiating visible light for positioning. These Japanese patents are used to direct the laser energy and do not teach the concurrent use of laser energy and electrosurgery energy.

U.S. Pat. No. 5,324,254 discloses a single laparoscopic instrument capable of supplying either laser radiation or electrosurgical energy. An electrosurgical electrode is provided at the distal end of the instrument for electrosurgical procedures. A side port located near the proximate end of the instrument allows for the passage of a laser fiberoptic bundle, thereby allowing for laser surgery. The patent does not teach the concurrent use of laser energy and electrosurgical energy in a synchronized manner.

An article entitled How Lasers Might Control Lightning Strikes, appearing in *Laser Focus World,* November 1993, pages 113–123, by Zhao, Xin Miao and Daniels, Jean-Claude, discloses how lasers establish an ionized pathway for electric arc transmission. Ordinary optical beams produce little ionization in air or an essentially weak plasma which can be used to direct electrical discharges.

The application of any form of atmospheric ionization to direct electrosurgical beams either statically or dynamically has not been disclosed in the prior technology.

SUMMARY OF THE INVENTION

A laser and electrosurgical system allows a surgeon to provide cutting, coagulating, and/or a combination thereof on tissue of a patient. The laser and electrosurgical system preferably has a handpiece with a proximal end to be held and controlled by the surgeon. A distal end may be included on the handpiece from which laser radiation and/or electrosurgical energy may be selectively or concurrently directed to the patient. The proximal and distal ends are most preferably along an axis. An electrosurgical electrode might extend from the distal end along the axis. A source energy for laser radiation most preferably is available at the proximal end and is controlled by the surgeon for delivery of laser radiation from the distal end toward the patient. A source of electrosurgical energy might also be available at the proximal end and may be controlled by the surgeon for transmission of electrosurgical energy from the electrosurgical electrode toward the patient.

A return path is provided for the electrosurgical energy. The return path is connected to receive at least a portion of the transmitted electrosurgical energy from the source of electrosurgical energy toward the patient. A return input for the source of electrosurgical energy is connected to the return path for furnishing a complete circuit between the electrosurgical electrode, the patient, and the source of electrosurgical energy.

A control may be connected to the source energy for laser radiation and to the source of electrosurgical energy for the selective or concurrent application of laser radiation and electrosurgical energy from the distal end.

The laser and electrosurgical system may have in the control an initiation circuit for the source energy for laser radiation, so laser radiation may be selectively delivered from the distal end slightly in advance of the delivery of the electrosurgical energy. The advance delivery of the laser radiation may be used to pinpoint the target tissue to be treated. The delivered laser radiation may also be used to create an ionized conductive pathway along which the electrosurgical energy will be guided.

The laser and electrosurgical system may be configured so the distal end and the electrosurgical electrode are preferably arranged geometrically relative to the handpiece to provide laser radiation essentially along the axis and from the distal end. This geometry provides for the combined concurrent application of the laser radiation and the electrosurgical energy. The ionized pathway is formed by the laser radiation from the distal end to the patient substantially along the axis to direct the electrosurgical energy.

The laser and electrosurgical system may provide a control which operates a mechanism to selectively distribute, in a predetermined pattern about the axis, the delivered laser radiation from the distal end.

The laser and electrosurgical system may include an electromagnetic radiation deflecting surface arranged to vibrate relative to the axis. This preferably forms a predetermined pattern to achieve a varying ionized conductive pathway generally along but slightly displaced from the axis for thereby directing electrosurgical energy in the predetermined pattern to the patient.

The laser and electrosurgical system may be configured such that the laser radiation is a beam and the mechanism includes a beam pattern deflector. The beam pattern deflector may be an acousto-optic modulator or arrangement of acousto-optic modulators to diffract, refract or reflect the beam.

The laser and electrosurgical system may include in the control for the source energy for laser radiation a power switch which may select between two levels of laser radiation energy delivery. The power switch may include a cutting laser radiation energy level and another level to provide for the ionized conductive pathway. The power switch may also include a time delay mechanism to interpose a preset time period between the initiation of cutting laser radiation and the subsequent delivery of electrosurgical energy for coagulation. The time delay should be sufficient to provide time for cutting with the laser radiation, followed by concurrent electrosurgical coagulation along the ionized conductive pathway to the laser cut tissue.

The laser and electrosurgical system may have the laser radiation energy within the visible, near-infrared and infrared light spectrum wavelengths. In one possible configuration the laser radiation source provides radiation of a wavelength in the range of between 0.3 to 10.6 microns for establishing through air the ionized conductive pathway as substantially collimated.

A wave guide may be used to deliver the laser radiation from the proximal end to beyond the distal end and generally along the axis. An array of wave guides may also be used to deliver the laser radiation from the proximal end to beyond the distal end and generally along the axis.

The laser and electrosurgical system may include a handpiece which is generally shaped like a pistol grip, where the pistol grip depends near the proximal end and is therefore at an angle to the axis which extends from the distal end in the direction which the electrode is pointed.

The laser and electrosurgical system may have an electrosurgical electrode which is flexible and elongate for endoscopic or laparoscopic use within a cannula passing through the patient's body wall and into a cavity therein.

The laser and electrosurgical system may have its control located on the handpiece between the proximal and distal ends. The control may also be located on a foot pedal.

The laser and electrosurgical system may have a source of electrosurgical energy which includes an electrosurgical generator and a return path which is carried on the handpiece for bipolar electrosurgery on the tissue of the patient. Alternatively, the return path may include a return pad connected to the patient for receiving electrosurgical energy during monopolar electrosurgery on the tissue of the patient.

A method for providing cutting, coagulating, and/or a combination thereof on tissue of a patient with a laser and electrosurgical system may include the following step of directing selectively and at least concurrently laser radiation and electrosurgical energy from a handpiece with its proximal and distal ends along an axis by aiming the distal end thereof along the axis from which laser radiation and electrosurgical energy may be at least in part concurrently directed. A further step might be controlling a source energy for laser radiation available at the proximal end of the handpiece by the surgeon for first delivering laser radiation from the distal end. Controlling a source of electrosurgical energy available at the proximal end of the handpiece by the surgeon for transmission of electrosurgical energy from a electrosurgical electrode at the distal end may be yet another step of the method. Then the step of connecting a control to a source energy for laser radiation and to a source of electrosurgical energy so the control is preferably arranged for the concurrent application of laser radiation and electrosurgical energy from the distal end.

The method can also include the additional step of initiating the laser radiation delivered from the distal end concurrently or slightly in advance of the delivery of the electrosurgical energy so that the laser radiation forms an ionized conductive pathway along which the electrosurgical energy will be guided for pinpointing the target tissue to be treated.

The method may include the additional step of guiding the electrosurgical energy by arranging the distal end and the electrosurgical electrode geometrically relative to the handpiece for providing laser radiation essentially along the axis and from the distal end for the combined concurrent application of the laser radiation and the electrosurgical energy. Then the added step of ionizing a conductive pathway with laser radiation from the distal end to the patient along the axis to direct the flow of electrosurgical energy is preferably performed.

The method may include the additional step of distributing the laser radiation available at the proximal end for delivery about the axis in a predetermined pattern from the distal end with a mechanism. In one possible configuration, there is an added step in which the mechanism can deflect the laser radiation to create a varying ionized conductive pathway with an electromagnetic radiation deflecting surface that vibrates in a predetermined pattern generally along but slightly displaced from the axis to direct electrosurgical energy in a predefined pattern on the patient's target tissue. In another possible approach, there are additional steps of delivering the laser radiation as a beam and varying an ionized conductive pathway by refracting or diffracting the laser radiation beam with the mechanism having a beam pattern deflector.

The method of initiating the laser radiation slightly in advance of the delivery of the electrosurgical energy may be augmented with the additional steps of controlling the laser radiation initially with a switch having two levels of delivery. A first level of delivery may be a cutting level and a second level may be an ionizing conductive pathway level. This may provide for delaying the subsequent delivery of electrosurgical energy for coagulation sufficiently for providing time for first cutting with the laser radiation and thereafter enabling, with the switch, the concurrent electrosurgical fulguration along the later ionized conductive pathway to the coagulate.

The method may also include the additional step of using laser radiation in the visible, near-infrared and infrared light spectrum wavelengths provided by the source of laser radiation. There may also be the additional step of using a wave guide or an array of wave guides for delivery of the laser radiation from the proximal end to beyond the distal end and generally along the axis.

The method may include the additional step of using the handpiece, which is generally shaped like a pistol grip, by aiming along the axis extending from the distal end in the direction in which the electrode is pointed while having the pistol grip at an angle ergonomically comfortable for surgery. The method may also include the additional step of flexing into position an elongate electrosurgical electrode for endoscopic or laparoscopic use in a cannula placed through the patient's body wall and into a cavity therein. There may be the additional step of using the control located on the handpiece between the proximal and distal ends, or using the control located on a foot pedal.

DETAILED DESCRIPTION OF THE INVENTION

Figure 1:
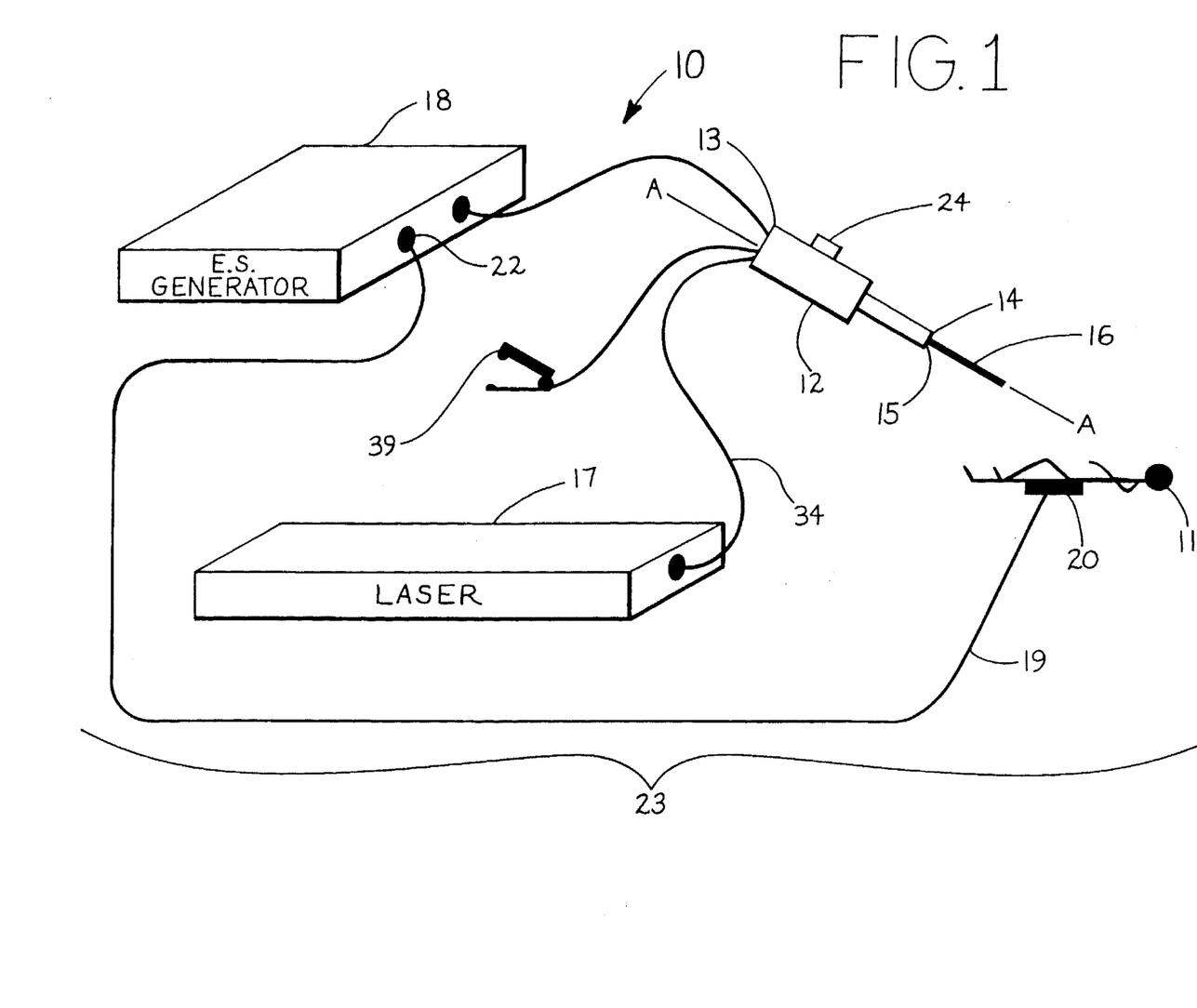
FIG. 1 is a schematic drawing of the laser and electrosurgical system showing a monopolar configuration of the elements.

A laser and electrosurgical system 10 is shown in perspective in FIG. 1 and allows a surgeon to provide cutting, coagulating, and/or a combination thereof on tissue of a patient 11. The laser and electrosurgical system 10 has a handpiece 12 with a proximal end 13 to be held and controlled by the surgeon. A distal end 14 on the handpiece 12 has a port 15 from which laser radiation and/or electrosurgical energy are selectively or concurrently directed to the patient 11. The proximal and distal ends 13 and 14 are along an axis "A". An electrosurgical electrode 16 extends from the distal end 14 along the axis "A". A source energy for laser radiation 17 preferably manufactured by Coherent, Inc., located in Palo Alto, Calif., and sold as model Infinity is connected to be available at the proximal end 13 and is controlled by the surgeon for delivery of laser radiation from the distal end 14 toward the patient 11. A source of electrosurgical energy 18 preferably manufactured by Valleylab, located in Boulder, Colo., and sold as model Force 40, is connected electrically to be available at the proximal end 13 and may be controlled by the surgeon for transmission of electrosurgical energy from the electrosurgical electrode 16 toward the patient 11.

Figure 2:
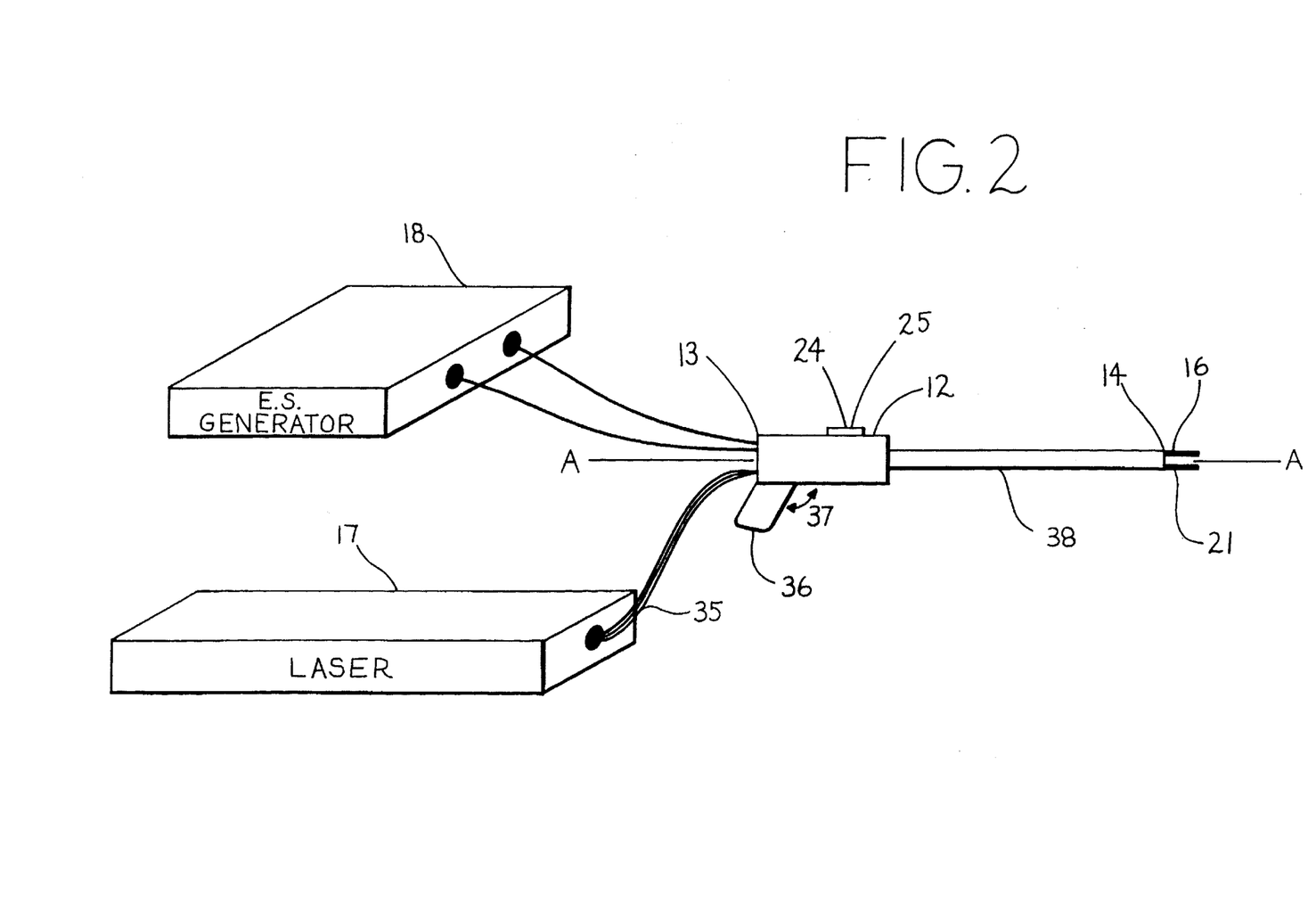
FIG. 2 is a schematic drawing of the laser and electrosurgical system showing a bipolar configuration of the elements.

A return path 19 is provided for the electrosurgical energy; the return path 19 may be in a monopolar or bipolar circuit as schematically shown in FIGS. 1 and 2, respectively. Specifically, in FIG. 1 there is a return pad 20 and in FIG. 2 there is a bipolar return electrode 21 each to complete their respective circuits. The return path 19 is connected to receive at least a portion of the transmitted electrosurgical energy from the source of electrosurgical energy 18 and then the patient 11. A return input 22 for the source of electrosurgical energy 18 is connected to the return path 19 for furnishing a complete circuit 23 between the electrosurgical electrode 16, the patient 11, and the source of electrosurgical energy 18.

A control 24 is connected to the source energy for laser radiation 17 and to the source of electrosurgical energy 18 for the selective or concurrent application of laser radiation and electrosurgical energy from the distal end 14. The advance delivery of the laser radiation may be used to pinpoint the target tissue to be treated when the laser radiation is within the visible spectrum. The delivered laser radiation is also used to create an ionized conductive pathway along which the electrosurgical energy will be guided.

Figure 3:
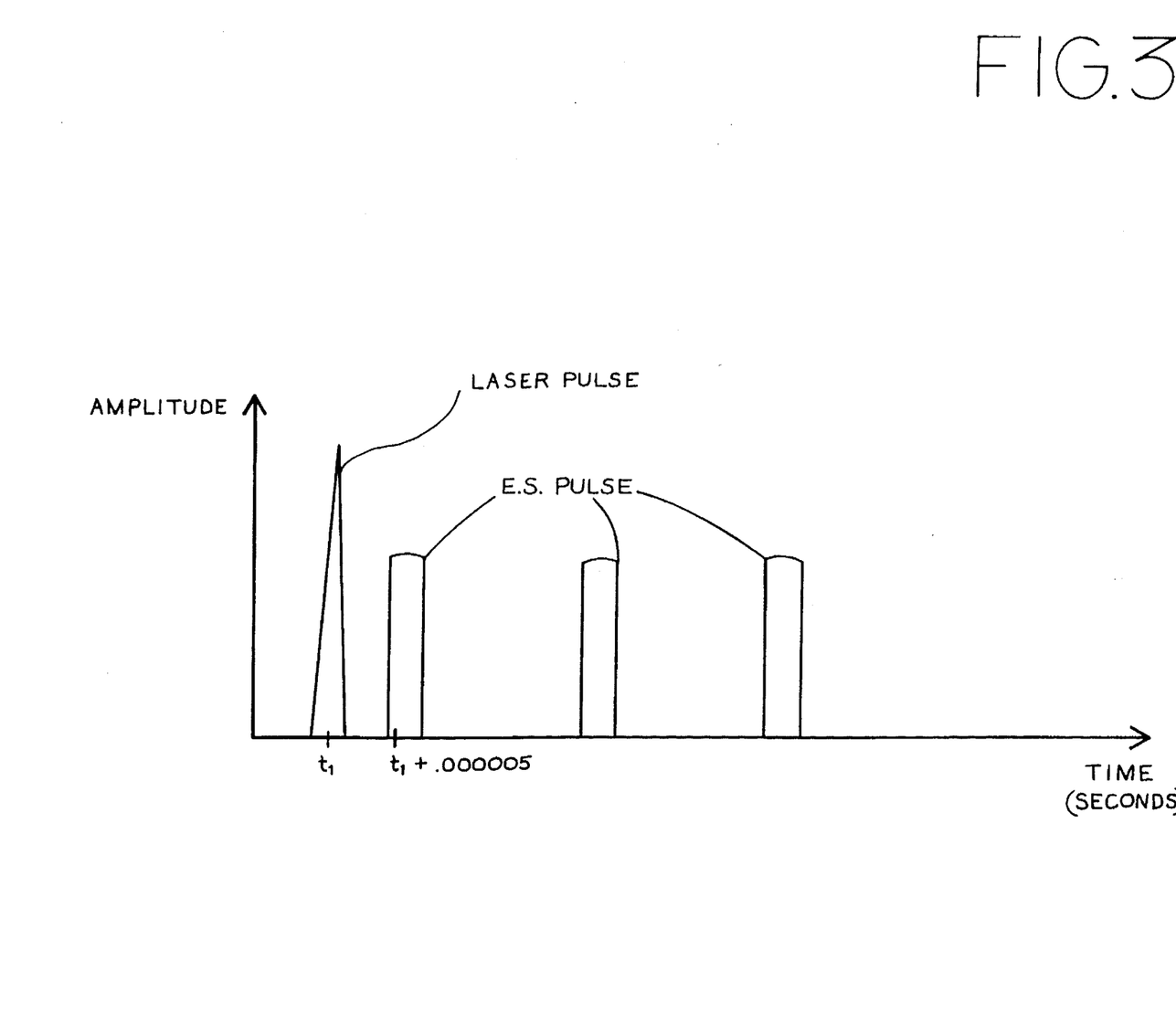
FIG. 3 is a pulse timing graph which illustrates the timing between a laser pulse and successive electrosurgical pulses during a coagulation mode.

The laser and electrosurgical system 10 has in the control 24 an initiation circuit 25 for the source energy for laser radiation 17, so laser radiation may be selectively delivered from the distal end 14 concurrently or slightly in advance of the delivery of the electrosurgical energy. The laser energy will be modulated at a rate between 10 Hz. and 31 kHz., and may be synchronized to deliver the pulse between zero and five microseconds ahead of the electrosurgical pulse. This allows the electrosurgical energy to follow the ionized pathway created by the laser energy. In FIG. 3, one possible pulse diagram is shown for the laser pulse and the electrosurgical pulse. The laser pulse occurs at $t_1$ and the electrosurgical pulse occurs at $t_1 + 0.000005$ seconds.

When the laser is being used to create an ionized pathway, the laser energy must be controlled in order to avoid undesired tissue effects. The duty cycle of the laser will be kept in the range of $10^{-5}$ to $10^{-8}$. Energy density delivered to any single area of tissue from the laser pulse should not exceed 26 J/cm$^2$ for wavelengths between 1.06 and 10.6 microns, and 17 J/cm$^2$ for wavelengths around and below 0.53 microns.

The laser and electrosurgical system 10 is configured so the distal end 14 and the electrosurgical electrode 16 are preferably arranged geometrically relative to the handpiece 12 to provide laser radiation essentially along the axis "A" and from the distal end 14. This geometry provides for the combined concurrent application of the laser radiation and the electrosurgical energy. The ionized pathway is formed by the laser radiation from the distal end 14 to the patient 11 substantially along the axis "A" to direct the electrosurgical energy therealong.

Figure 4:
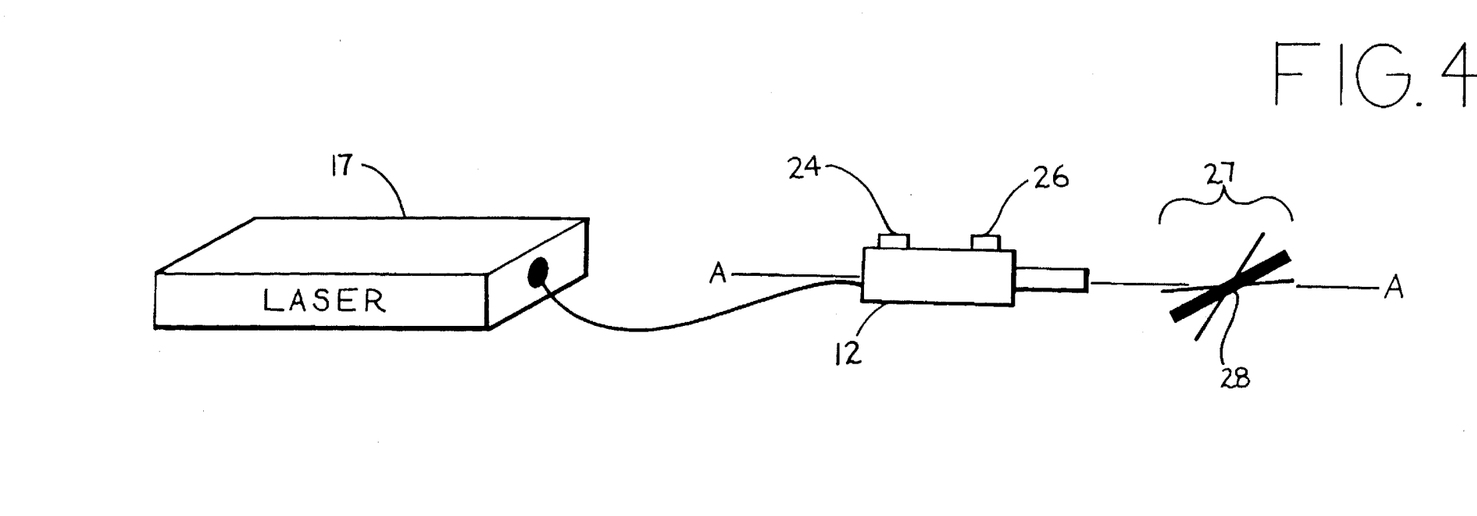
FIG. 4 is a schematic drawing of a portion of the laser and electrosurgical system which illustrates the use of an electromagnetic radiation deflecting surface.
Figure 5:
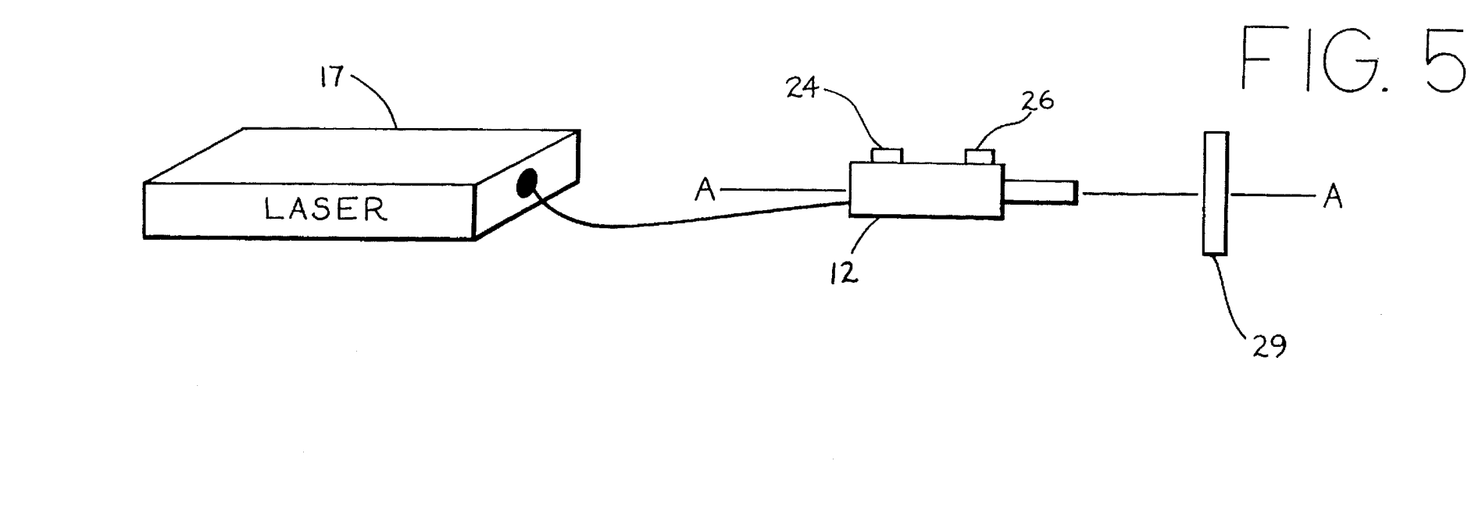
FIG. 5 is a schematic drawing of a portion of the laser and electrosurgical system which illustrates the use of an acousto-optic modulator.

The laser and electrosurgical system 10 provides a button 26 which operates a mechanism 27, see FIG. 4, to selectively distribute in a predetermined pattern about the axis "A" the laser radiation from the distal end 14. The mechanism 27 includes an electromagnetic radiation deflecting surface 28 arranged to vibrate relative to the axis "A". This forms a predetermined pattern to achieve a varying ionized conductive pathway generally along but slightly displaced from the axis "A" for thereby directing electrosurgical energy in the predetermined pattern to the patient 11. The mechanism 27 may alternatively include a beam pattern deflector 29. The beam pattern deflector 29 may be an acousto-optic modulator or arrangement of acousto-optic modulators to diffract, refract or reflect the laser radiation.

Figure 6:
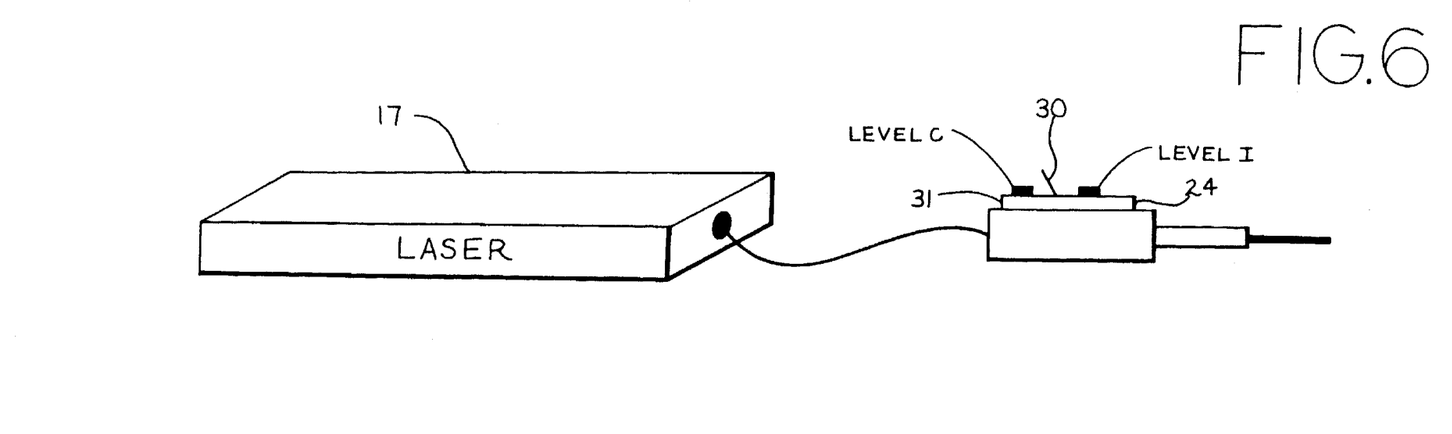
FIG. 6 is a schematic drawing of a portion of the laser and electrosurgical system which illustrates the use of a power switch.
Figure 7:
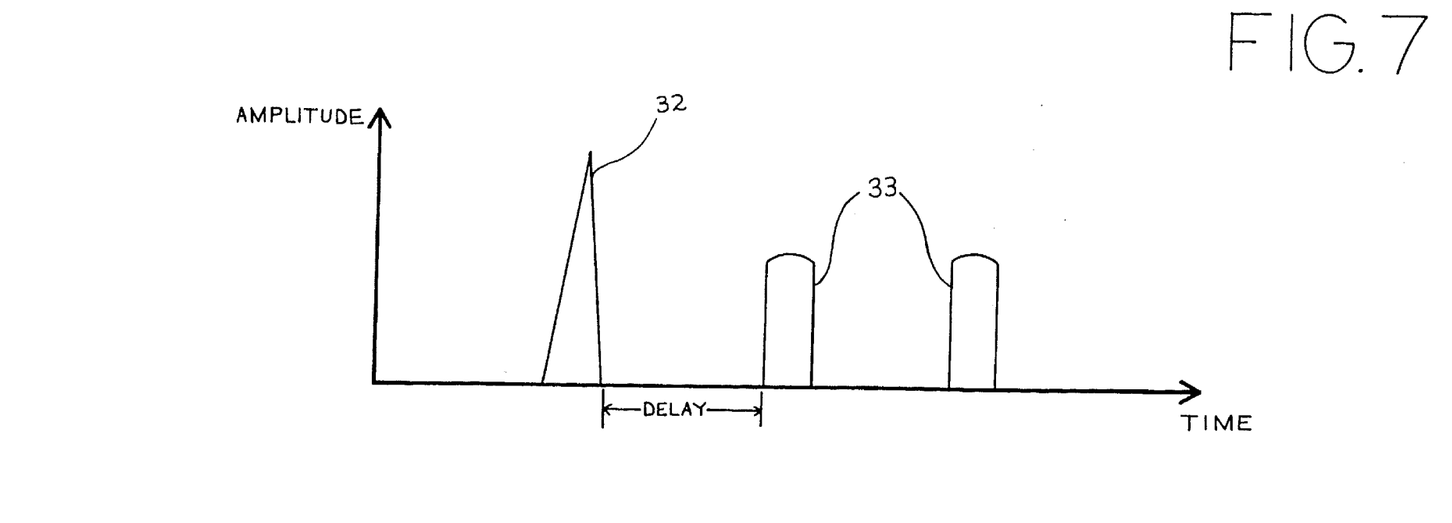
FIG. 7 is a pulse timing graph which illustrates the timing between a laser pulse and successive electrosurgical pulses during a laser cut mode.

In another alternate, the laser and electrosurgical system 10 includes in the control 24 for the source energy for laser radiation 17 a power switch 30 which may select between two levels of laser radiation energy delivery. This may be accomplished by changing the duty cycle of the laser. The power switch 30 includes a cutting laser radiation energy level "C" and another level "I" to provide for the ionized conductive pathway. The power switch 30 also includes an electronic time delay mechanism 31 to interpose a preset time period, shown in FIG. 7, between the initiation of cutting laser radiation 32 and the subsequent delivery of electrosurgical energy 33 for coagulation. The time delay should be sufficient to provide time for cutting with the laser radiation, followed by concurrent electrosurgical coagulation along the ionized conductive pathway to the laser cut tissue.

The laser and electrosurgical system 10 has the laser radiation energy within the range of visible, near-infrared and infrared light spectrum wavelengths. The laser radiation source 17 provides radiation of wavelengths in the range of between 0.3 to 10.6 microns for establishing through air the ionized conductive pathway as substantially collimated.

A wave guide 34, shown in FIG. 1, is used to deliver the laser radiation from the proximal end 13 to beyond the distal end 14 and generally along the axis "A". An array of wave guides 35, shown in FIG. 2 may alternatively be used to deliver the laser radiation from the proximal end 13 to beyond the distal end 14 and generally along the axis "A".

The laser and electrosurgical system 10 includes on the handpiece 12 a pistol grip 36 which depends near the proximal end 13 and is therefore at an angle 37 to the axis "A" which extends from the distal end 14 in the direction which the electrode 16 is pointed.

The laser and electrosurgical system 10 has alternatively in FIG. 2 an electrosurgical electrode support 38 which is flexible and elongate for endoscopic or laparoscopic use within a cannula (not shown) passing through the patient's body wall and into a cavity therein.

The laser and electrosurgical system 10 has its control located on the handpiece between the proximal and distal ends 13 and 14. The control may also be located on the pistol grip 36 or at a foot pedal 39.

A method for providing cutting, coagulating, and/or a combination thereof on tissue of the patient 11 with a laser and electrosurgical system 10 includes the following step of directing selectively and at least concurrently laser radiation and electrosurgical energy from the handpiece 12 with its proximal and distal ends, 13 and 14, along an axis "A" by aiming the distal end 14 thereof along the axis "A" from which laser radiation and electrosurgical energy may be at least in part concurrently directed. A further step might be controlling the source energy for laser radiation 17 available at the proximal end 13 of the handpiece by the surgeon for first delivering laser radiation from the distal end 14. Controlling a source of electrosurgical energy available at the proximal end 13 of the handpiece 12 by the surgeon for transmission of electrosurgical energy from a electrosurgical electrode 16 at the distal end 14 may be yet another step of the method. Then may follow the step of connecting the control 24 to a source energy for laser radiation 17 and to a source of electrosurgical energy 18 so the control is preferably arranged for the concurrent application of laser radiation and electrosurgical energy from the distal end 14.

The method also includes the additional step of initiating the laser radiation delivered from the distal end 14 concurrently or slightly in advance of the delivery of the electrosurgical energy so that the laser radiation forms an ionized conductive pathway along which the electrosurgical energy will be guided for pinpointing the target tissue to be treated.

The method includes the additional step of guiding the electrosurgical energy by arranging the distal end 14 and the electrosurgical electrode 16 geometrically relative to the handpiece 12 for providing laser radiation essentially along the axis "A" and from the distal end 14 for the combined concurrent application of the laser radiation and the electrosurgical energy. Then the added step of ionizing a conductive pathway with laser radiation from the distal end 14 to the patient 11 along the axis "A" to direct the flow of electrosurgical energy is performed.

The method includes the additional step of distributing the laser radiation available at the proximal end for delivery about the axis "A" in a predetermined pattern from the distal end 14 with the mechanism 27. In one possible variation, there is an added step in which the mechanism 27 can deflect the laser radiation to create a varying ionized conductive pathway with an electromagnetic radiation deflecting surface 28 that vibrates in a predetermined pattern generally along but slightly displaced from the axis "A" to direct electrosurgical energy in a predefined pattern on the patient's 11 target tissue. In another possible approach, there are additional steps of delivering the laser radiation as a beam and varying an ionized conductive pathway by refracting or diffracting the laser radiation beam with the mechanism 27 having a beam pattern deflector 29.

The method of initiating the laser radiation slightly in advance of the delivery of the electrosurgical energy is augmented with the additional steps of controlling the laser radiation initially with the switch 30 having two levels of delivery. A first level of delivery "C" may be a cutting level and a second level "I" may be an ionizing conductive pathway level. This may provide for delaying the subsequent delivery of electrosurgical energy for coagulation sufficiently for providing time for first cutting with the laser radiation and thereafter enabling, with the switch, the concurrent electrosurgical fulguration along the later ionized conductive pathway to the coagulate.

The method also includes the additional step of using laser radiation in the visible, near-infrared and infrared light spectrum wavelengths provided by the source of laser radiation 17. There may also be the additional step of using the wave guide 34 or the array of wave guides 35 for delivery of the laser radiation from the proximal end 13 to beyond the distal end 14 and generally along the axis "A".

The method includes the additional step of using the handpiece, which is generally shaped like the pistol grip 36, by aiming along the axis "A" extending from the distal end 14 in the direction in which the electrode 16 is pointed while having the pistol grip 16 at an angle 37 ergonomically comfortable for surgery. The method also includes the additional step of flexing into position the elongate electrosurgical electrode support 38 for endoscopic or laparoscopic use in the cannula placed through the patient's body wall and into a cavity therein. There is the additional step of using the control 24 located on the handpiece 12 between the proximal and distal ends 13 and 14, or controlling with a foot pedal 39.

The claims which follow seek to cover the described embodiments and their equivalents. The concept in its broadest scope covers the apparatus and methods for concurrent and simultaneous application of laser and electrosurgical energy. It is to be understood that the concept is subject to many modifications without departing from the spirit and scope of the claims as recited herein.

What is claimed is:

1. A laser and electrosurgical system for a surgeon to use for cutting and coagulating tissue of a patient, the system comprising:

a handpiece having a proximal end to be held and controlled by the surgeon and a distal end from which laser radiation and electrosurgical energy may be directed to the patient;

at least one electrosurgical electrode on the handpiece and extending from the distal end;

a source of laser radiation connected to the proximal end by a waveguide, and the laser radiation transmitted from the proximal end to the distal end through another waveguide in the handpiece, and controlled by the surgeon for delivery of laser radiation from the distal end toward the patient;

a source of electrosurgical energy connected to the proximal end by an electrically conductive cable, and the electrosurgical energy transmitted from the proximal end to the electrode by an electrically conductive element in the handpiece, and controlled by the surgeon for transmission of electrosurgical energy from the electrosurgical electrode toward the patient, and an initiation circuit connected to the source of laser radiation and connected to the source of electrosurgical energy, the initiation circuit used for sequencing the delivery of laser radiation and electrosurgical energy to the patient, wherein the laser radiation has sufficient power to ionize a path between the distal end and the tissue of the patient, and the electrode is positioned near the path of the laser radiation such that the electrosurgical energy is conducted along the ionized path.

2. The laser and electrosurgical system of claim 1 wherein the source of laser radiation provides radiation of a wavelength in the range of between 0.3 to 10.6 microns for establishing the ionized conductive pathway.

3. The laser and electrosurgical system of claim 1 wherein a wave guide within the handpiece delivers the laser radiation from the proximal end to the distal end.

4. The laser and electrosurgical system of claim 1 wherein an array of wave guides within the handpiece deliver the laser radiation from the proximal end to the distal end.

5. A laser and electrosurgical system for a surgeon to use for cutting and coagulating the tissue of a patient, the system comprising:

a handpiece having a proximal end to be held and controlled by the surgeon end a distal end from which laser radiation and electrosurgical energy may be directed to the patient;

at least one electrosurgical electrode on the handpiece and extending from the distal end;

a source of laser radiation connected to the proximal end by a waveguide, and the laser radiation transmitted from the proximal end to the distal end through a waveguide in the handpiece, and controlled by the surgeon for delivery of laser radiation from the distal end toward the patient, the source of laser radiation having sufficient power to ionize a conductive pathway from the distal end to the tissue of the patient, and wherein the electrode is positioned near the path of the laser radiation;

a source of electrosurgical energy connected to the proximal end by an electrically conductive cable, and the electrosurgical energy transmitted from the proximal end to the electrode by an electrically conductive element in the handpiece, and controlled by the surgeon for transmission of electrosurgical energy from the electrosurgical electrode toward the patient;

a control connected to the source of laser radiation and to the source of electrosurgical energy for the selective application of laser radiation and electrosurgical energy from the distal end, and a power switch in the control for selecting between two levels of laser radiation energy delivery, the power switch including a cutting laser radiation energy level and the ionized conductive pathway level of laser radiation energy.

6. The laser and electrosurgical system of claim 5 wherein the power switch includes a time delay mechanism to interpose a preset time period between the initiation of cutting laser radiation and the subsequent delivery of electrosurgical energy for coagulation, the preset time sufficient to provide time for cutting with the laser radiation, the power switch thereafter enables concurrent electrosurgical coagulation along the ionized conductive pathway to the laser cut tissue.

7. A method for cutting and coagulating tissue of a patient with a laser and electrosurgical system, the method including the steps of:

supplying laser radiation and electrosurgical energy to a handpiece having a distal end;

sequencing the delivery of laser radiation and electrosurgical energy from the distal end for first creating an ionized path between the distal end and the tissue using a burst of laser radiation, and before the ionized path dissipates, conducting electrosurgical energy along the ionized pathway.

\* \* \* \* \*